(12) United States Patent
Eom et al.

(10) Patent No.: US 9,072,460 B2
(45) Date of Patent: Jul. 7, 2015

(54) OPTICAL COHERENCE TOMOGRAPHY DEVICE AND OPTICAL COHERENCE TOMOGRAPHY METHOD

(75) Inventors: Tae Joong Eom, Gwangju (KR); In-Won Lee, Gwangju (KR); Hoon-Seop Kim, Gwangju (KR)

(73) Assignee: HUVITZ CO., LTD., Gunpo-Si (KR)

( * ) Notice: Subject to any disclaimer, the term of this patent is extended or adjusted under 35 U.S.C. 154(b) by 3 days.

(21) Appl. No.: 14/124,287

(22) PCT Filed: May 30, 2012

(86) PCT No.: PCT/KR2012/004242
§ 371 (c)(1),
(2), (4) Date: Dec. 6, 2013

(87) PCT Pub. No.: WO2012/169740
PCT Pub. Date: Dec. 13, 2012

(65) Prior Publication Data
US 2014/0125951 A1    May 8, 2014

(30) Foreign Application Priority Data
Jun. 9, 2011 (KR) .................. 10-2011-0055492

(51) Int. Cl.
*A61B 3/14* (2006.01)
*G06K 9/00* (2006.01)
(Continued)

(52) U.S. Cl.
CPC ............ *A61B 3/102* (2013.01); *G01B 9/02028* (2013.01); *G01B 9/02007* (2013.01); *G01B 9/02027* (2013.01); *G01B 9/02091* (2013.01); *G01B 9/02063* (2013.01)

(58) Field of Classification Search
CPC .......... G01B 9/02091; G01B 9/02028; G01B 9/02027; G01B 9/02007; G01B 2290/45; A61B 5/0073; A61B 3/102; A61B 3/14; A61B 3/1225
USPC .......... 351/205, 206, 210, 221; 356/477, 479, 356/497; 382/131; 600/407, 425
See application file for complete search history.

(56) References Cited

U.S. PATENT DOCUMENTS

| | | | |
|---|---|---|---|
| 7,400,410 B2 | 7/2008 | Baker et al. | 356/498 |
| 2008/0175465 A1 | 7/2008 | Jiang et al. | 382/131 |
| 2011/0103658 A1 | 5/2011 | Davis et al. | 382/128 |

FOREIGN PATENT DOCUMENTS

| | | |
|---|---|---|
| JP | 2004-503278 A | 2/2004 |
| JP | 2004-294432 A | 10/2004 |

(Continued)

OTHER PUBLICATIONS

European Search Report dated Oct. 24, 2014 issued in Application No. 12 79 6926.9.

(Continued)

*Primary Examiner* — Mahidere Sahle
(74) *Attorney, Agent, or Firm* — Ked & Associates, LLP (57) ABSTRACT

The present invention relates to an optical coherence tomography device and an optical coherence tomography method using same for capturing the cornea and the retina of the eye by using light sources in respectively different wavelength ranges. According to the present invention, included are two light sources, a first interferometer and a second interferometer for generating respectively different interference patterns by the light outputted from each of the light sources, and interference pattern detection means for detecting an interference pattern occurring in each interferometer.

20 Claims, 5 Drawing Sheets

(51) Int. Cl.
  *A61B 3/10* (2006.01)
  *G01B 9/02* (2006.01)

(56) References Cited

FOREIGN PATENT DOCUMENTS

| JP | 2009-264787 A | 11/2009 |
| KR | 10-2008-0076303 A | 8/2008 |
| WO | WO 2010/011656 A1 | 1/2010 |
| WO | WO 2010/073655 A1 | 7/2010 |

OTHER PUBLICATIONS

International Search Report dated Nov. 16, 2012 issued in Application No. PCT/KR2012/004242.

Fig 6 ptical Coherence Tomography Device and Optical Coherence Tomography Method

CROSS-REFERENCE TO RELATED PATENT APPLICATIONS

This application is a U.S National Stage Application under 35 U.S.C. §371 of PCT Application No. PCT/KR2012/004242, filed May 30, 2012, which claims priority to Korean Patent Application No. 10-2011-0055492, filed Jun. 9, 2011, whose entire disclosures are hereby incorporated by reference.

TECHNICAL FIELD

The present invention relates to an optical coherence tomography device and an optical coherence tomography method, and more specifically, to an optical coherence tomography device and an optical coherence tomography method that allow for simultaneous imaging of the cornea and retina of an eye using light sources with different wavelength ranges from each other.

BACKGROUND ART

An optical coherence tomography (OCT) device is an optical tomography device that images the cross section of a biological tissue in a non-invasive way using a light source with a near-IR (Infra Red) (a wavelength ranging from 0.6 to 1.3). The OCT is a new imaging technology that is being researched for addressing several problems, such as harmful to human bodies, high price, and low resolution, shown by existing measuring devices including X-ray computed tomography (CT), ultrasound imaging, and magnetic resonance imaging.

The OCT device operates based on the Michelson interferometer. In an OCT device, a light signal generated from a light source is split into two optical signals by an optical coupler, and the two optical signals, respectively, are input to a reference arm and a sample arm. Reference light that is back from the reference arm and sample light that is backward scattered at the sample arm meet again, causing an interference signal. The interference signal is processed to be thereby imaged.

The OCT device has a higher resolution than that of the existing ultrasound imaging device. The OCT device may image the inside of an object in a non-surgical manner and provides many advantages, such as being able to perform real-time tomography and being manufactured at low price.

Thanks to high resolution and non-invasive imaging, the OCT device is recently used a lot for ophthalmological purposes. However, the existing commercial OCT device is produced as an independent device dedicated for tomographing a cornea or retina, or even an OCT device for research, in order to obtain tomographed images of the retina and cornea of an eye using the same, is forced to first photograph one of the retina and cornea, and after refocusing, presume the imaging of the other. However, refocusing takes a while, thus causing a testee's inconvenience. Accordingly, a need exists for an OCT device that may simultaneously image the retina and cornea of an eye.

DETAILED DESCRIPTION OF INVENTION

Technical Problems

The present invention has been designed to address the above-described problems of the prior art, and an object of the present invention is to provide an optical coherence tomography device and method that enables simultaneous imaging of the retina and cornea of an eye.

Solutions to the Problems

To address the above-described problems, the present invention provides an optical coherence tomography device comprising a first light source outputting first light; a second light source outputting second light having a longer wavelength range than the first light; a first optical coupler splitting the first light into first reference light and first sample light and outputting the first reference light and the first sample light; a second optical coupler splitting the second light into second reference light and second sample light and outputting the second reference light and the second sample light; a first reference mirror onto which the first reference light is incident and reflecting the first reference light; a second reference mirror onto which the second reference light is incident and reflecting the second reference light; a wavelength combining means combining wavelengths of the first sample light and the second sample light; a first wavelength selective transmitting means reflecting the first sample light incident from the wavelength combining means at a predetermined angle and transmitting the second sample light; an optical path changing means reflecting the first sample light reflected by the first wavelength selective transmitting means at a predetermined angle; a second wavelength selective transmitting means transmitting the second sample light that has passed through the first wavelength selective transmitting means and reflecting the first sample light reflected by the optical path changing means at a predetermined angle; a first lens positioned over an optical path of the first sample light between the first wavelength selective transmitting means and the second wavelength selective transmitting means and concentrating the first sample light; a second lens transforming the first sample light reflected by the second wavelength selective transmitting means into parallel light, outputting the parallel light to a first portion of an object to be imaged and concentrating the second sample light that has passed through the second wavelength selective transmitting means to a second portion of the object; a first interference pattern detecting means detecting an interference pattern that is generated by a combination of returning light of the first sample light scattered or reflected at the first portion and reflected light of the first reference light reflected by the first reference mirror; and a second interference pattern detecting means detecting an interference pattern that is generated by a combination of returning light of the second sample light scattered or reflected at the second portion and reflected light of the second reference light reflected by the second reference mirror.

According to another embodiment, the present invention provides an optical coherence tomography device comprising: a first light source outputting first light; a second light source outputting second light having a longer wavelength range than the first light; a first optical coupler splitting the first light into first reference light and first sample light and outputting the first reference light and the first sample light; a second optical coupler splitting the second light into second reference light and second sample light and outputting the second reference light and the second sample light; a first reference mirror onto which the first reference light is incident and reflecting the first reference light; a second reference mirror onto which the second reference light is incident and reflecting the second reference light; an optical path changing means reflecting the first sample light coming from the first optical coupler at a predetermined angle; a wavelength selective transmitting means reflecting the first sample light reflected by the optical path changing means at a predetermined angle and transmitting the second sample light coming from the second optical coupler; a first lens positioned over an optical path of the first sample light between the first optical coupler and the wavelength selective transmitting means and concentrating the first sample light; a second lens transforming the first sample light reflected by the wavelength selective transmitting means into parallel light, outputting the parallel light to a first portion of an object to be imaged and concentrating the second sample light that has passed through the wavelength selective transmitting means to a second portion of the object; a first interference pattern detecting means detecting an interference pattern that is generated by a combination of returning light of the first sample light scattered or reflected at the first portion and reflected light of the first reference light reflected by the first reference mirror; and a second interference pattern detecting means detecting an interference pattern that is generated by a combination of returning light of the second sample light scattered or reflected at the second portion and reflected light of the second reference light reflected by the second reference mirror.

Further, the present invention provides an optical coherence tomography method comprising: outputting first light from a first light source and second light from a second light source, the second light having a longer wavelength range than the first light; splitting the first light into first reference light and first sample light and splitting the second light into second reference light and second sample light; reflecting the first reference light to a first reference mirror and the second reference light to a second reference mirror; combining wavelengths of the first sample light and the second sample light using a wavelength combining means; changing an optical path of the first sample light to pass through a first lens using a first wavelength selective transmitting means; allowing the first sample light that has passed through the first lens to pass through the second lens using a second wavelength selective transmitting means so that the first sample light is scattered or reflected at a first portion of an object to be imaged; allowing the second sample light to pass through the second lens so that the second sample light is scattered or reflected at a second portion of the object; splitting returning light of the first sample light and returning light of the second sample light using the wavelength combining means; generating an interference pattern by combining reflected light of the first reference light with returning light of the first sample light; and generating an interference pattern by combining reflected light of the second reference light with returning light of the second sample light.

Effects of Invention

According to an embodiment of the present invention, the retina and cornea of an eye may be simultaneously imaged, thus reducing the image time.

According to an embodiment of the present invention, even a single XY scanner enables simultaneous imaging of a retina and cornea, so that the device may be cost-downed or made compact. Further, as compared with when using two independent XY scanners, use of such a single XY scanner may relatively reduce errors in measured positions.

Further, according to an embodiment of the present invention, an optical fiber Bragg grating is provided, so that interference patterns generated from light sources with different wavelength ranges from each other may be precisely detected without interference between the patterns.

BEST MODE

Hereinafter, preferred embodiments of the present invention are described with reference to the accompanying drawings. The same reference numerals may denote the same or substantially the same elements throughout the specification and the drawings. When determined to make the subject matter unnecessarily unclear, the detailed description of the prior art will be skipped.

Figure 1:
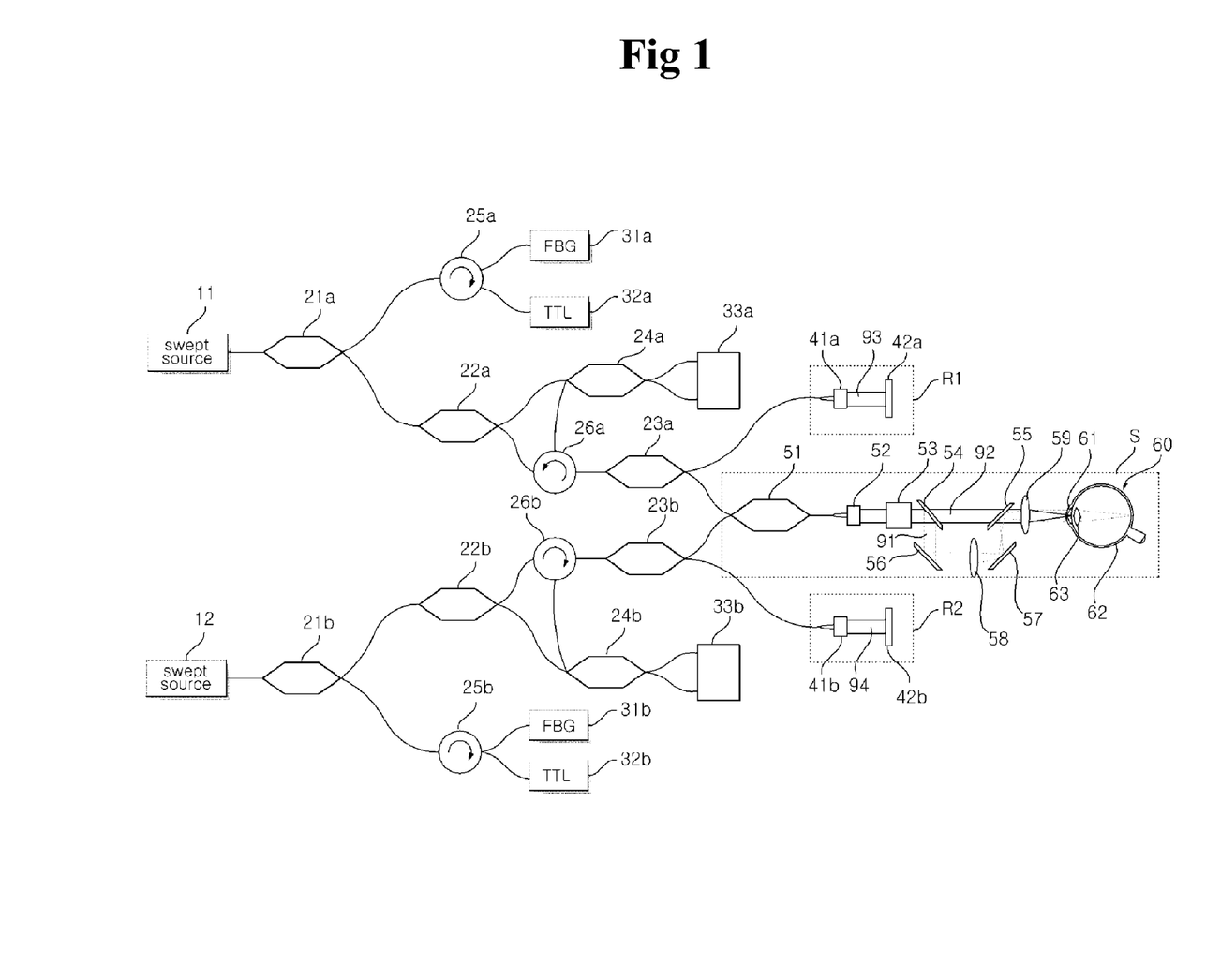
FIG. 1 is a view illustrating the overall configuration of an optical coherence tomography device according to a first embodiment of the present invention.
Figure 2:
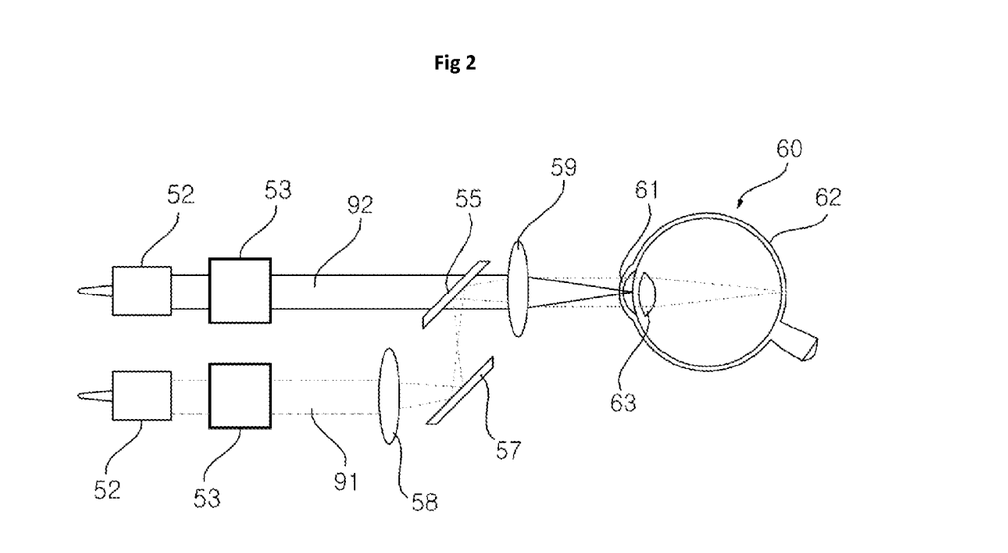
FIG. 2 is an expanded view of the sample arm of FIG. 1.
Figure 3:
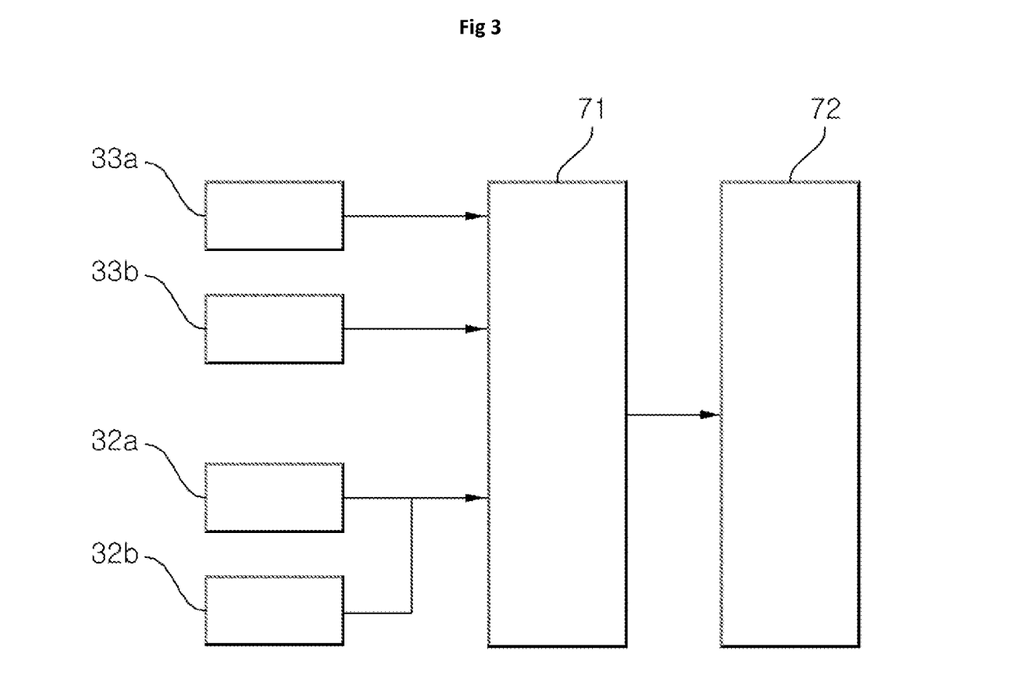
FIG. 3 is a view illustrating the configuration of a digitizer and a signal processing unit for processing a signal having an interference pattern in an optical coherence tomography device according to the first embodiment of the present invention.

FIG. 1 is a view illustrating the overall configuration of an optical coherence tomography device according to a first embodiment of the present invention, FIG. 2 is an expanded view of the sample arm of FIG. 1, and FIG. 3 is a view illustrating the configuration of a digitizer and a signal processing unit for processing a signal having an interference pattern in an optical coherence tomography device according to the first embodiment of the present invention. FIG. 1 illustrates an optical coherence tomography device according to the first embodiment of the present invention and an eye imaged by the optical coherence tomography device. Hereinafter, a configuration for imaging the retina and cornea of an eye using the optical coherence tomography device according to the first embodiment of the present invention is described.

Referring to FIGS. 1 to 3, the optical coherence tomography device according to the first embodiment of the present invention includes two light sources 11 and 12, a first interferometer and a second interferometer that respectively generate different interference patterns by light output from the light sources 11 and 12, and an interference pattern detecting means that detects an interference pattern generated from each of the interferometers. The first interferometer includes a first reference arm R1, and the second interferometer includes a second reference arm R2. The first and second interferometers share a sample arm S. The first and second interferometers are symmetrical to each other with respect to the sample arm S. Light beams, respectively output from the light sources 11 and 12 and passing through the first and second interferometers, propagate along the same path. Further, the light beams respectively output from the light sources 11 and 12 are incident onto the retina 62 and cornea 61 of an eye 60 through the single sample arm S, and then, scattered or reflected, thereby to generate independent interference patterns. Accordingly, by the optical coherence tomography device according to the first embodiment of the present invention, the retina 62 and the cornea 61 may be simultaneously imaged using one sample arm S.

The light sources 11 and 12 include a first light source 11 and a second light source 12. The first light source 11 and the second light source 12 are preferably wavelength swept lasers. The first light source 11 outputs a first light beam, and the second light source 12 outputs a second light beam having a wavelength of a different wavelength range from that of the first light beam. The first light source 11 is for imaging a deep portion of an object to be imaged, which is positioned beyond another portion of the object having relatively low light absorption owing to the moisture of the object, and the second light source 12 is for imaging relatively a surface portion of the object. It is preferable that the first light source 11 has a wavelength range with a relatively low light absorption with respect to moisture than the second light source 12.

In case the optical coherence tomography device according to the present invention is used for tomographing the eye 60, the first and second light sources 11 and 12 preferably have wavelengths of a near-infra red. Further, the wavelength of the first and second light sources 11 and 12 influences the depth-directional resolution of a tomographed image, and accordingly, the light sources preferably have broad wavelength ranges. In this embodiment, the first light source 11 outputs a first light beam for imaging the retina 62, and the second light source 12 outputs a second light beam for imaging the cornea 61. In order for the first light beam to reach the retina 62, the first light beam needs to pass through the vitreous body of the eye 60, and thus, the first light beam preferably has a wavelength range shoter than the second light beam. For example, the first light source 11 may be a wavelength swept laser having a wavelength range of 1.0 μm, and the second light source 12 may be a wavelength swept laser having a wavelength range of 1.3 μm. Alternatively, the first light source 11 may be a wavelength swept laser having a wavelength range of 0.8 μm, and the second light source 12 may be a wavelength swept laser having a wavelength range of 1.0 μm or 1.3 μm. The bandwidth of light output from the first light source 11 and the second light source 12 may be set to about 100.

Meanwhile, depending on the type of an object to be imaged and portion of the object, which is to be measured, light sources having different wavelengths from the above-selected wavelengths of the light sources according to this embodiment may be chosen. However, even in such case, the first light source 11 and the second light source 12 should have wavelengths of different bands from each other.

The first interferometer and the second interferometer have the same components and have the same optical path. The first interferometer includes first, second, third, and fourth optical couplers 21, 22, 23, and 24, first and second optical circulators 25 and 26, a reference mirror 42, a wavelength combining means 51, an XY scanner 53, wavelength selective transmitting means 54 and 55, optical path changing means 56 and 57, and lenses 58 and 59.

Specifically, the first interferometer includes a first optical coupler 21a for splitting light coming from the first light source 11, a second optical coupler 22a for splitting light coming from the first optical coupler 21a, a third optical coupler 23a for splitting light coming from the second optical coupler 22a into first reference light 93 and first sample light 91, a first reference arm R1 for reflecting the first reference light 93 to generate an interference pattern, a sample arm S for allowing the first sample light 91 to be incident onto the eye 60 and then scattering or reflecting the first sample light 91, a fourth optical coupler 24a for combining light coming from the second optical coupler 22 and the combination light of the first reference light 93 and the first sample light 91 and transferring the combined light to an optical detector 33, a second optical circulator 26a for transferring light coming from the second optical coupler 22a to the third optical coupler 23a and transferring light coming from the third optical coupler 23a to the fourth optical coupler 24a, and a first optical circulator 25a for transferring light coming from the first optical coupler 21a to an optical fiber Bragg grating 31a and transferring light reflected by the optical fiber Bragg grating 31a to a trigger 32a.

The second interferometer includes a first optical coupler 21b for splitting light coming from the second light source 12, a second optical coupler 22b for splitting light coming from the first optical coupler 21b, a third optical coupler 23b for splitting light coming from the second optical coupler 22b into second reference light 94b and second sample light 92b, a second reference arm R2b for reflecting the second reference light 94b to generate an interference pattern, a sample arm S for allowing the second sample light 92b to be incident onto the eye 60b and then scattering or reflecting the second sample light 92b, a fourth optical coupler 24b for combining light coming from the second optical coupler 22b and the combination light of the second reference light 94 and the second sample light 92 and transferring the combined light to the optical detector 33, a second optical circulator 26b for transferring light exiting from the second optical coupler 22b to the third optical coupler 23b and transferring light exiting from the third optical coupler 23b to the fourth optical coupler 24b, and a first optical circulator 25b for light exiting from the first optical coupler 21b to the optical fiber Bragg grating 31b and transferring light reflected by the optical fiber Bragg grating 31b to a trigger 32b.

The first reference arm R1 includes a collimator 41a for transforming the first reference light 93 into parallel light and a reference mirror 42a for reflecting the first reference light 93.

The second reference arm R2 includes a collimator 41b for transforming the second reference light 94 into parallel light and a reference mirror 42b for reflecting the second reference light 94.

The sample arm S includes a wavelength combining means for combining the wavelength of the first sample light 91 coming from the third optical coupler 23a of the first interferometer with the wavelength of the second sample light 92 coming from the third optical coupler 23b of the second interferometer, a collimator 52 for transforming light coming from the wavelength combining means 51 into parallel light, an XY scanner 53 for adjusting the traveling direction of the parallel light, a first wavelength selective transmitting means 54 for reflecting the first sample light 91 at a predetermined angle and transmitting the second sample light 92, first and second optical path changing means 56 and 57 for reflecting the first sample light 91 at a predetermined angle, a second wavelength selective transmitting means 55 for transmitting the second sample light 92 that has passed through the first wavelength selective transmitting means 54 and reflecting the first sample light 91 reflected by the first and second optical path changing means 56 and 57 at a predetermined angle, a first lens 58 positioned over an optical path of the first sample light 91 between the first wavelength selective transmitting means 54 and the second wavelength selective transmitting means 55 to concentrate the first sample light 91, and a second lens 59 for transforming the first sample light 91 reflected from the second wavelength selective transmitting means 55 into parallel light, transferring the parallel light to the retina 62, and concentrating the second sample light 92 that has passed through the second wavelength selective transmitting means 55 to the cornea 61.

The wavelength combining means 51 combines the incident first sample light 91 and the second sample light 92 that have different wavelengths from each other into one and splits, depending on wavelengths, returning light of the first sample light 91 and returning light of the second sample light 92, which have different wavelengths from each other. In the instant embodiment, as the wavelength combining means 51, a WDM (Wavelength Division Multiplexing) coupler is used.

The XY scanner 53 adjusts the travelling directions of the first sample light 91 and the second sample light 92 with respect to an X-axis direction and a Y-axis direction and performs X-axis directional (horizontal direction) scan and Y-axis directional (vertical direction) scan of the eye 60.

The wavelength selective transmitting means 54 and 55 selectively transmit the first sample light 91 and the second sample light 92, which are incident, mixed with each other, depending on wavelengths or reflect the light at a predetermined angle. In the present embodiment, as the wavelength selective transmitting means, dichroic mirrors are used, which reflect the first sample light 91 at 90 degrees while transmitting the second sample light 92.

The first optical path changing means 56 and the second optical path changing means 57 guide the first sample light 91 reflected by the first wavelength selective transmitting means 54 to the second wavelength selective transmitting means 55 by changing the traveling direction of the first sample light 91. In this embodiment, as the first and second optical path changing means 56 and 57, a pair of mirrors for reflecting the first sample light 1 at 90 degrees is used.

The first lens 58 and the second lens 59 concentrate the incident first sample light 91 and second sample light 92 to a specific focal distance or transform the concentrated light into parallel light.

The first sample light 91 and the second sample light 92, combined by the wavelength combining means 51, are split by the wavelength selective transmitting means 54 and 55 due to the internal structure of the eye 60. In order for parallel light to be concentrated to a specific point, the parallel light needs to pass through an odd number of lenses. Accordingly, an odd number of lenses need to be provided over the optical path of the second sample light 92, which has been transformed into parallel light, so that the second sample light 92 may be concentrated to the cornea 61. However, on the optical path through which the first sample light 91 travels to the retina 62, an eye lens 63 is positioned which serves as a lens that concentrates the first sample light 91, and thus, for the first sample light 91 to be concentrated to the retina 62, an even number of lenses should be provided over the optical path of the first sample light 91. Accordingly, after the first sample light 91 is rendered to travel along a different optical path, the first lens 58 is positioned on the optical path, so that the second sample light 92 may enter the eye 60 after passing through an odd number of lenses, and the first sample light 91 may enter the eye 60 after passing through an even number of lenses.

Next, the interference pattern detecting means includes an optical fiber Bragg grating 31, a trigger 32, an optical detector 33, and a digitizer 71.

The optical fiber Bragg grating 31 reflects only light having a specific wavelength and transmits light having the other wavelengths. The trigger 32, when light reflected from the optical fiber Bragg grating 31 coming thereto, generates a trigger signal. The optical detector 33 detects an interference pattern that is generated by a combination of the reflected light of the reference light 93 and 94 reflected by the reference mirror 42 and the returning light of the sample light 91 and 92 that is scattered or reflected by the retina 62 or cornea 61 of the eye 60. The interference pattern signal detected by the optical detector 33 is transferred to the digitizer 71 and is transformed into an electrical signal. In this embodiment, as the optical detector 33, a balanced receiver is used. By the above-described configuration, the first light and the second light respectively output from the light sources 11 and 12 are reflected by the optical fiber Bragg grating 31, and accordingly, a trigger signal is generated by the trigger 32. Thus, an interference pattern generated from the light sources 11 and 12 having different wavelength ranges from each other may be precisely detected using one digitizer 71.

The signal processing unit 72 images the planar structure of the retina 62 and the cornea 61 by signal-processing and image-processing the electrical signal generated by the digitizer 71. The signal processing unit 72 may be implemented as a personal computer.

Hereinafter, the principle in which an interference pattern is generated by an optical coherence tomography device according to the first embodiment of the present invention is described referring to the above-described components.

First light output from the first light source 11 is split by the first optical coupler 21a and is incident onto the second optical coupler 22a and the first optical circulator 25a. The first light incident onto the second optical coupler 22a comes to the third optical coupler 23a via the second optical circulator 26a. The first light is split by the third optical coupler 23a into first reference light 93 that is to be incident onto the first reference arm R1 and first sample light 91 that is to be incident onto the sample arm S. The first reference light 93 is transformed into parallel light by the collimator 41a and is then reflected by the first reference mirror 42a and is then incident onto the third optical coupler 23a. The first sample light 91 is wavelength-combined with the second sample light 92 that is to be described later, while passing through the wavelength combining means 51, then coming to the sample arm S.

Second light output from the second light source 12 is split by the first optical coupler 21b and is incident onto the second optical coupler 22b and the first optical circulator 25b. The second light incident onto the second optical coupler 22b comes to the third optical coupler 23b via the second optical circulator 26b. The second light incident onto the third optical coupler 23b is split into second reference light 94 that is to be incident onto the second reference arm R2 and second sample light that is to be incident onto the sample arm S. The second reference light 94 is transformed by the collimator 41b into parallel light and is then reflected by the second reference mirror 42b, then incident onto the third optical coupler 23b. The second sample light 92 is wavelength-combined with the first sample light 91 while passing through the wavelength combining means 51 and is incident onto the sample arm S.

The first sample light 91 and the second sample light 92, which have been wavelength combined by the wavelength combining means 51 is transformed by the collimator 52 into parallel light and then travels to the first wavelength selective transmitting means 54 via the XY scanner 53. The first wavelength selective transmitting means 54 and the second wavelength selective transmitting means 55 reflect the first sample light 91 that has a short wavelength and transmits the second sample light 92 that has a long wavelength. Accordingly the second sample light 92 sequentially passes through the first wavelength selective transmitting means 54 and the second wavelength selective transmitting means 55 and is then concentrated into the cornea 61 of the eye 60 by the second lens 59. In contrast, the first sample light 91 is reflected by the first wavelength selective transmitting means 54 at 90 degrees. At this time, the traveling direction of the first sample light 91 and the second sample light 92 which are incident by the first wavelength selective transmitting means 54 is adjusted by the XY scanner 53. The first sample light 91 which has been reflected by the first wavelength selective transmitting means 54 is sequentially reflected by the first optical path changing means 56 and the second optical path changing means 57 at 90 degrees and is then guided to the second wavelength selective transmitting means 55. The first sample light 91 is concentrated into the first lens 58 before incident to the second wavelength selective transmitting means 55 and is then transformed into parallel light by the second lens 59, and is then concentrated into the retina 62 of the eye 60 by the eye lens 63.

The first and second sample light 91 and 92, which have been incident onto the cornea 61 of retina 62 of the eye 60, is scattered or reflected due to a difference in the refractive index between different cells or tissues present in the cornea 61 or the retina 62. The returning light of the second sample light which has been backward scattered by the cornea 61 passes through the second lens 59, the first wavelength selective transmitting means 54, the XY scanner 53, and the collimator 52 back to the wavelength combining means 51. The returning light of the first sample light 91 which has been backward scattered by the retina 62 passes through the second lens 59, the second wavelength selective transmitting means 55, the second optical path changing means 57, the first optical path changing means 56, the first wavelength selective transmitting means 54, the XY scanner 53, and the collimator 52 back to the wavelength combining means 51.

The returning light of the first sample light 91 and the returning light of the second sample light 92 are split by the wavelength combining means 51 and then are respectively incident onto the third optical coupler 23a of the first interferometer and the third optical coupler 23b of the second interferometer. The returning light of the first sample light 91 is combined with the reflected light of the first reference light thereby to generate an interference pattern signal of the retina 62. The returning light of the second sample light 92 is combined with the reflected light of the second reference light thereby to generate an interference pattern signal of the cornea 61. The interference pattern signal of the retina 62 and the interference pattern signal of the cornea 61 are incident onto the optical detector 33 via the second optical circulator 26 and the fourth optical coupler 24, and the optical detector 33 detects the interference patterns of the retina 62 and the cornea 61.

The interference pattern signal of the retina 62 and the interference pattern signal of the cornea 61 are input to the digitizer 71, and the digitizer 71 differentiates the retina interference pattern signal and the cornea interference pattern signal from each other by a trigger signal generated by the trigger 32 and transforms them into electrical signals. The electrical signals are processed by the signal processing unit 72 and are thus transformed into planar structure images of the retina 62 and the cornea 61.

Thereafter, the first light source 11 and the second light source 12 are swept, thereby sequentially detecting and imaging the interference patterns.

Figure 4:
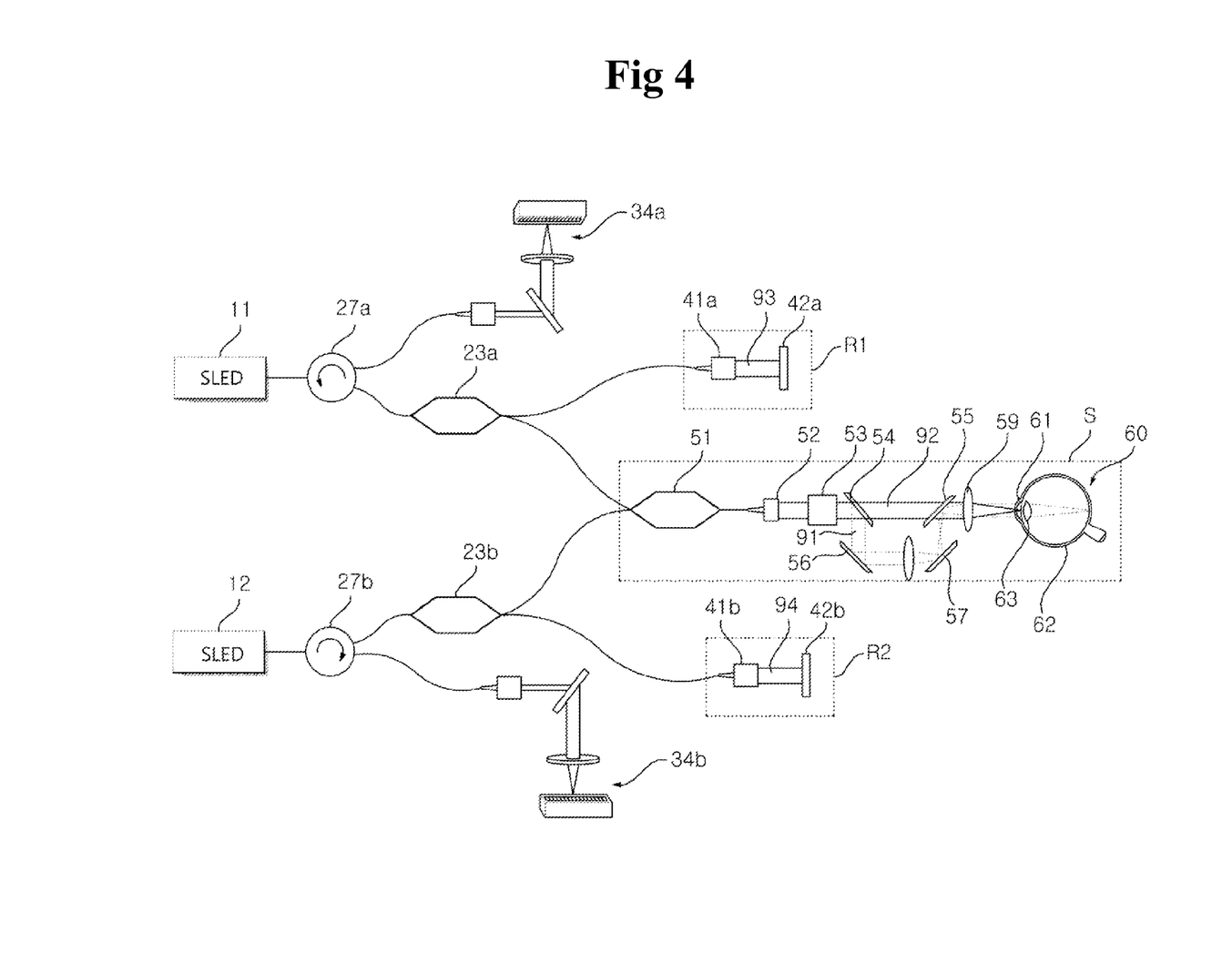
FIG. 4 is a view illustrating the overall configuration of an optical coherence tomography device according to a second embodiment of the present invention.

FIG. 4 is a view illustrating the overall configuration of an optical coherence tomography device according to a second embodiment of the present invention. The embodiment to be described in connection with FIG. 4 is similar to the embodiment described in connection with FIG. 1 except that broadband light sources are used as the light sources and a spectrometer is used for detecting an interference pattern. Hereinafter, the description will focus on the differences in configuration. In FIG. 4, the same or corresponding components to those described according to the first embodiment are referred to by the same denotations, and the description of the components that have been described in connection with the first embodiment are skipped.

Referring too, the optical coherence tomography device according to the first embodiment of the present invention includes two light sources 11 and 12, a first interferometer and a second interferometer respectively generating different interference patterns from each other by light output from the light sources 11 and 12, respectively, and an interference pattern detecting means for detecting an interference pattern generated from each interferometer.

The first interferometer includes a first reference arm, and the second interferometer includes a second reference arm. The first interferometer and the second interferometer share one sample arm so that light beams respectively output from the light sources are incident onto the retina and cornea of an eye through the single sample arm and are scattered or reflected, thereby generating their respective interference patterns. Accordingly, the optical coherence tomography device according to the first embodiment of the present invention may image the retina and cornea at the same time using one sample arm. From such a point of view, the basic principle of operation according to the second embodiment is the same as the first embodiment.

However, in this embodiment, as the first light source 11 and the second light source 12, broadband light sources are used, such as SLEDs (Super luminescent LEDs). Accordingly, no need exists for varying the wavelength in order to photograph the retina and cornea.

As the broadband light sources are used as the light sources 11 and 12, a spectrometer 34 is used to detect interference patterns that are generated by the first interferometer and the second interferometer.

Figure 5:
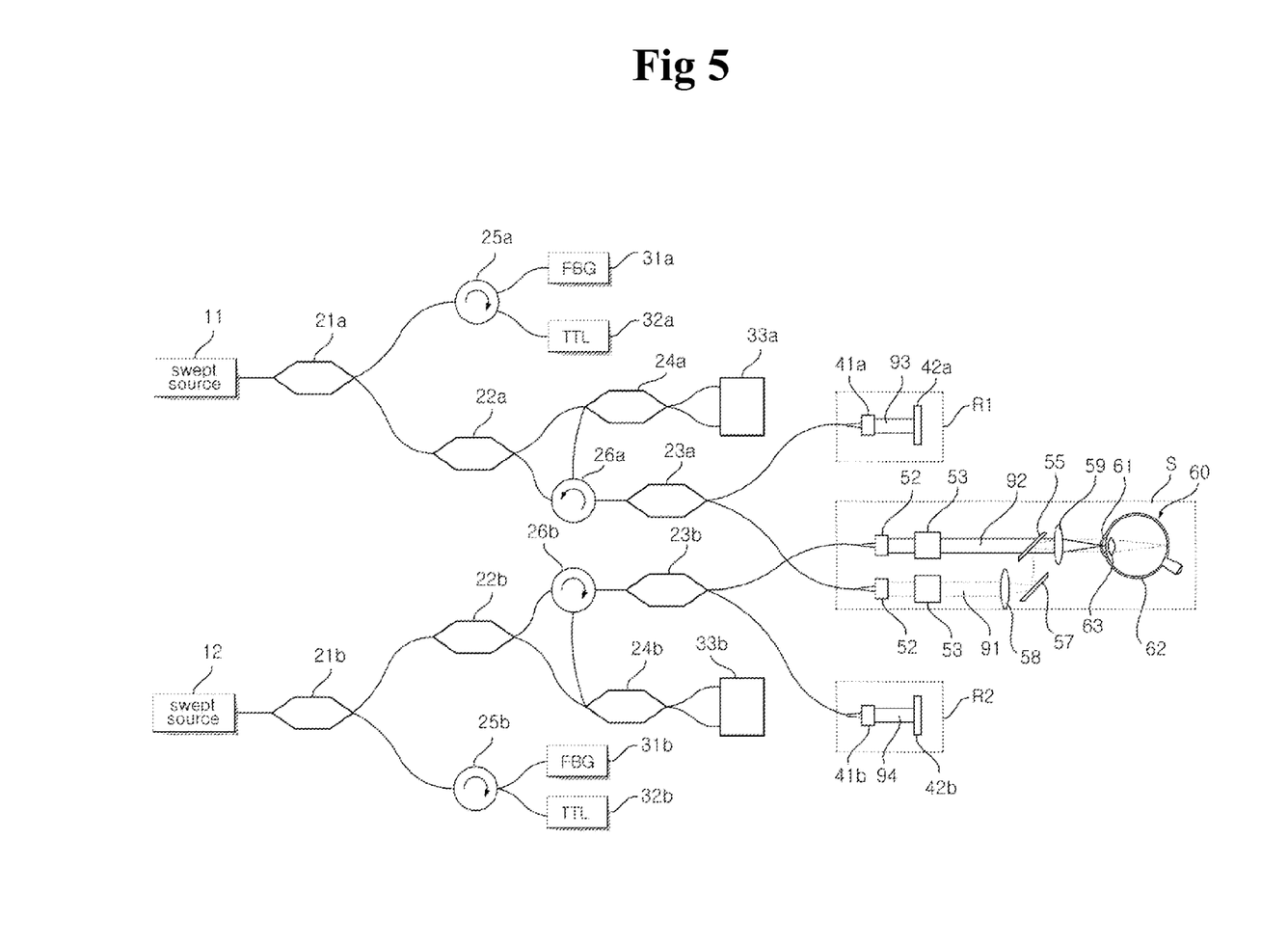
FIG. 5 is a view illustrating the overall configuration of an optical coherence tomography device according to a third embodiment of the present invention.
Figure 6:
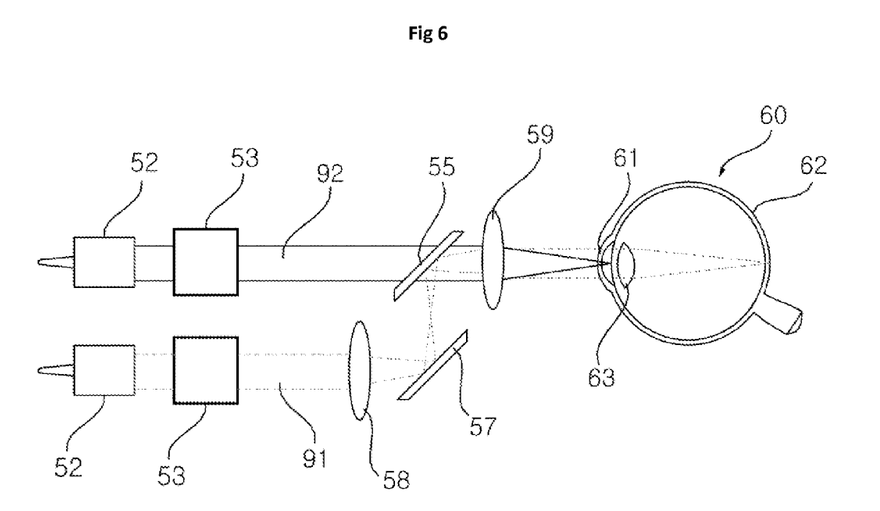
FIG. 6 is an expanded view of the sample arm of FIG. 5.

FIG. 5 is a view illustrating the overall configuration of an optical coherence tomography device according to a third embodiment of the present invention. FIG. 6 is an expanded view of the sample arm of FIG. 5. The embodiment to be described in connection with FIG. 5 is similar to the embodiment described in connection with FIG. 1 except for the configuration of the sample arm, and thus, the description will focus on the differences in configuration. The same or corresponding components to those described according to the embodiment described in connection with FIG. 1 are referred to by the same denotations, and the description of the components that have been described in connection with the first embodiment are skipped.

Referring to FIGS. 5 and 6, the sample arm S includes a collimator 52 for transforming first sample light 91 coming from a third optical coupler 23a and second sample light 92 coming from the third optical coupler 23a into parallel light, an XY scanner 53 for adjusting the travelling direction of the parallel light, an optical path changing means 57 for reflecting the first sample light 91 at a predetermined angle, a wavelength selective transmitting means 55 for transmitting the second sample light 92 and reflecting the first sample light 91 reflected by the optical path changing means 57 at a predetermined angle, a first lens 58 positioned over the optical path of the first sample light 91 between the third optical coupler 23a and the wavelength selective transmitting means 55 to concentrate the first sample light 91, and a second lens 59 for transforming the first sample light 91 reflected by the wavelength selective transmitting means into parallel light, directing the parallel light to the retina 62, and concentrating the second sample light 92 that has passed through the wavelength selective transmitting means 55 to the cornea 61.

As configured above, the sample arm S according to this embodiment lacks the wavelength combining means 51 according to the first embodiment, and the first sample light 91 and the second sample light 92 are independently incident onto the sample arm S and exit the sample arm S.

In this embodiment, the first sample light 91 and the second sample light 92 are independently incident onto the sample arm S. Accordingly, two XY scanners 53 are provided to adjust the travelling paths of the first sample light 91 and the second sample light 92.

Although the first sample light 91 and the second sample light 92 are independently incident onto the sample arm S, the first sample light 91 and the second sample light 92 are radiated to the eye 60 through the same path, so that the cornea 61 and the retina 62 may be photographed at the same time.

The first light output from the first light source 11 is split into first reference light 93 and first sample light 91 by the third optical coupler 23a, and the first sample light 91 is incident onto the sample arm S. The first sample light 91 that has been incident onto the first sample light 91 passes through the collimator 52, the XY scanner 53, and the first lens and then is sequentially reflected at 90 degrees by the optical path changing means 57 and the wavelength selective transmitting means 55. Then, the first sample light 91 passes through the second lens 59 and is then backward scattered by the retina 62. The returning light of the first sample light 91 that has been backward scattered by the retina 62 is incident back onto the third optical coupler 23a of the first interferometer along the counter-path of the path along which the first sample light 91 is incident onto the retina 62.

The second light output from the second light source 12 is split by the third optical coupler 23b into second reference light 94 and second sample light 92. The second sample light 92 is incident onto the sample arm S. The second sample light 92 incident onto the sample arm S passes through the collimator 52, the XY scanner 53, the wavelength selective transmitting means 55, and the second lens 59 and is backward scattered by the cornea 61. The returning light of the second sample light 92 backward scattered by the cornea 61 is incident back onto the third optical coupler 23b of the second interferometer along the counter-path of the path along which the second sample light 92 is incident onto the cornea 61.

The returning light of the first sample light 91 is combined with the reflected light of the first reference light 93 reflected by the reference mirror 42a, thereby to generate an interference pattern signal of the retina 62. The returning light of the second sample light 92 is combined with the reflected light of the second reference light 94 reflected by the reference mirror 42b, thereby generating an interference pattern signal of the cornea 61. The interference pattern signal of the retina 62 and the interference pattern signal of the cornea 61 are incident onto the optical detector 33 via the second optical circulator 26 and the fourth optical coupler 24, and the optical detector 33 detects interference patterns of the retina 62 and the cornea 61.

Although embodiments of the present invention have been described merely as examples, it will be understood by those of ordinary skill in that art that various changes or modifications may be made thereto without departing from the essential features of the present invention. Accordingly, the embodiments disclosed herein should not be construed as limited thereto, and are rather provided for illustrative purposes of the present invention. The scope of the present invention should be interpreted by the following claims and all equivalents thereof should be construed as included in the scope of the present invention.

The invention claimed is:

1. An optical coherence tomography device comprising:
   a first light source outputting first light;
   a second light source outputting second light having a longer wavelength range than the first light;
   a first optical coupler splitting the first light into first reference light and first sample light and outputting the first reference light and the first sample light;
   a second optical coupler splitting the second light into second reference light and second sample light and outputting the second reference light and the second sample light;
   a first reference mirror onto which the first reference light is incident and reflecting the first reference light;
   a second reference mirror onto which the second reference light is incident and reflecting the second reference light;
   a wavelength combining means combining wavelengths of the first sample light and the second sample light;
   a first wavelength selective transmitting means reflecting the first sample light incident from the wavelength combining means at a predetermined angle and transmitting the second sample light;
   an optical path changing means reflecting the first sample light reflected by the first wavelength selective transmitting means at a predetermined angle;
   a second wavelength selective transmitting means transmitting the second sample light that has passed through the first wavelength selective transmitting means and reflecting the first sample light reflected by the optical path changing means at a predetermined angle;
   a first lens positioned over an optical path of the first sample light between the first wavelength selective transmitting means and the second wavelength selective transmitting means and concentrating the first sample light;
   a second lens transforming the first sample light reflected by the second wavelength selective transmitting means into parallel light, outputting the parallel light to a first portion of an object to be imaged and concentrating the second sample light that has passed through the second wavelength selective transmitting means to a second portion of the object;
   a first interference pattern detecting means detecting an interference pattern that is generated by a combination of returning light of the first sample light scattered or reflected at the first portion and reflected light of the first reference light reflected by the first reference mirror; and
   a second interference pattern detecting means detecting an interference pattern that is generated by a combination of returning light of the second sample light scattered or reflected at the second portion and reflected light of the second reference light reflected by the second reference mirror.

2. The optical coherence tomography device of claim 1, further comprising an XY scanner adjusting travelling directions of the first sample light and the second sample light at the same time.

3. The optical coherence tomography device of claim 1, wherein the first wavelength selective transmitting means and the second wavelength selective transmitting means each are a Dichroic mirror that selectively transmits or reflects, at a predetermined angle, light depending on a wavelength.

4. The optical coherence tomography device of claim 1, wherein the first wavelength selective transmitting means and the second wavelength selective transmitting means reflect the first sample light at 90 degrees, and wherein the optical path changing means includes a first mirror and a second mirror for reflecting the first sample light at 90 degrees.

5. The optical coherence tomography device of claim 1, wherein the wavelength combining means is a WDM (Wavelength Division Multiplexing) coupler.

6. The optical coherence tomography device of claim 1, wherein the first light source and the second light source are wavelength swept lasers.

7. The optical coherence tomography device of claim 6, wherein the first light source is a wavelength swept laser having a wavelength range of 1.0 μm, and the second light source is a wavelength swept laser having a wavelength range of 1.3 μm.

8. The optical coherence tomography device of claim 1, wherein the first light source and the second light source are broadband light sources, and the interference pattern detecting means is a spectrometer.

9. An optical coherence tomography device comprising:
a first light source outputting first light;
a second light source outputting second light having a longer wavelength range than the first light;
a first optical coupler splitting the first light into first reference light and first sample light and outputting the first reference light and the first sample light;
a second optical coupler splitting the second light into second reference light and second sample light and outputting the second reference light and the second sample light;
a first reference mirror onto which the first reference light is incident and reflecting the first reference light;
a second reference mirror onto which the second reference light is incident and reflecting the second reference light;
an optical path changing means reflecting the first sample light coming from the first optical coupler at a predetermined angle;
a wavelength selective transmitting means reflecting the first sample light reflected by the optical path changing means at a predetermined angle and transmitting the second sample light coming from the second optical coupler;
a first lens positioned over an optical path of the first sample light between the first optical coupler and the wavelength selective transmitting means and concentrating the first sample light;
a second lens transforming the first sample light reflected by the wavelength selective transmitting means into parallel light, outputting the parallel light to a first portion of an object to be imaged and concentrating the second sample light that has passed through the wavelength selective transmitting means to a second portion of the object;
a first interference pattern detecting means detecting an interference pattern that is generated by a combination of returning light of the first sample light scattered or reflected at the first portion and reflected light of the first reference light reflected by the first reference mirror; and
a second interference pattern detecting means detecting an interference pattern that is generated by a combination of returning light of the second sample light scattered or reflected at the second portion and reflected light of the second reference light reflected by the second reference mirror.

10. The optical coherence tomography device of claim 9, further comprising a first XY scanner adjusting a travelling direction of the first sample light and a second XY scanner adjusting a travelling direction of the second sample light.

11. The optical coherence tomography device of claim 9, wherein the wavelength selective transmitting means is a Dichroic mirror that selectively transmits light or reflects, at a predetermined angle, light depending on a wavelength.

12. The optical coherence tomography device of claim 9, wherein the wavelength selective transmitting means reflects the first sample light at 90 degrees, and wherein the optical path changing means is a mirror that reflects the first sample light at 90 degrees.

13. The optical coherence tomography device of claim 9, wherein the first light source and the second light source are wavelength swept lasers.

14. The optical coherence tomography device of claim 12, wherein the first light source is a wavelength swept laser having a wavelength range of 1.0 μm, and the second light source is a wavelength swept laser having a wavelength range of 1.3 μm.

15. The optical coherence tomography device of claim 9, wherein the first light source and the second light source are broadband light sources, and the interference pattern detecting means is a spectrometer.

16. An optical coherence tomography method comprising:
outputting first light from a first light source and second light from a second light source, the second light having a longer wavelength range than the first light; splitting the first light into first reference light and first sample light and splitting the second light into second reference light and second sample light; reflecting the first reference light to a first reference mirror and the second reference light to a second reference mirror; combining wavelengths of the first sample light and the second sample light using a wavelength combining means; changing an optical path of the first sample light to pass through a first lens using a first wavelength selective transmitting means; allowing the first sample light that has passed through the first lens to pass through a second lens using a second wavelength selective transmitting means so that the first sample light is scattered or reflected at a first portion of an object to be imaged; allowing the second sample light to pass through the second lens so that the second sample light is scattered or reflected at a second portion of the object; splitting returning light of the first sample light and returning light of the second sample light using the wavelength combining means; generating an interference pattern by combining reflected light of the first reference light with returning light of the first sample light; and generating an interference pattern by combining reflected light of the second reference light with returning light of the second sample light.

17. The optical coherence tomography method of claim 16, further comprising adjusting travelling directions of the first sample light and the second sample light at the same time using an XY scanner.

18. The optical coherence tomography method of claim 16, wherein the first wavelength selective transmitting means and the second wavelength selective transmitting means each are a Dichroic mirror that selectively transmits or reflects, at a predetermined angle, light depending on a wavelength.

19. The optical coherence tomography method of claim 16, wherein the wavelength combining means is a WDM (Wavelength Division Multiplexing) coupler.

20. The optical coherence tomography method of claim 16, wherein the first light source and the second light source are wavelength swept lasers.

* * * * *